US010791977B2

(12) United States Patent
Choi

(10) Patent No.: US 10,791,977 B2
(45) Date of Patent: Oct. 6, 2020

(54) LASER LANCING DEVICE

(71) Applicant: LAMEDITECH CO., LTD., Seoul (KR)

(72) Inventor: Jong Seok Choi, Incheon (KR)

(*) Notice: Subject to any disclaimer, the term of this patent is extended or adjusted under 35 U.S.C. 154(b) by 144 days.

(21) Appl. No.: 16/018,965

(22) Filed: Jun. 26, 2018

(65) Prior Publication Data
US 2019/0274608 A1 Sep. 12, 2019

(30) Foreign Application Priority Data

Mar. 9, 2018 (KR) .................. 10-2018-0028241

(51) Int. Cl.
*A61B 5/151* (2006.01)
*A61B 5/15* (2006.01)
(Continued)

(52) U.S. Cl.
CPC .... *A61B 5/15136* (2013.01); *A61B 5/150022* (2013.01); *A61B 5/150129* (2013.01); *A61B 5/15138* (2013.01); *A61B 5/150748* (2013.01); *A61B 5/150824* (2013.01); *A61B 5/150954* (2013.01); *A61B 5/489* (2013.01); *A61B 18/203* (2013.01); *A61B 2017/00057* (2013.01); *A61B 2017/00407* (2013.01); *A61B 2017/00424* (2013.01); *A61B 2017/00765* (2013.01); *A61B 2017/22079* (2013.01); *A61B 2018/00017* (2013.01); *A61B 2018/00029* (2013.01); *A61B 2018/00196* (2013.01); *A61B 2018/00404* (2013.01); *A61B 2018/00458* (2013.01); *A61B 2018/00601* (2013.01); *A61B 2018/00613* (2013.01); *A61B 2018/00791* (2013.01);
(Continued)

(58) Field of Classification Search
None
See application file for complete search history.

(56) References Cited

U.S. PATENT DOCUMENTS 5,947,957 A 9/1999 Morris
6,790,205 B1 9/2004 Yamazaki et al.
(Continued)

FOREIGN PATENT DOCUMENTS

EP 1997435 A1 12/2008
EP 2153792 A1 2/2010
(Continued)

OTHER PUBLICATIONS

European Search Report for EP application No. 18179899.2 dated Dec. 20, 2018.

*Primary Examiner* — Brian T Gedeon
(74) *Attorney, Agent, or Firm* — Leepi

(57) ABSTRACT

The laser lancing device in accordance with an exemplary embodiment includes: a main body; a laser resonator located within the main body and configured to generate a laser and output the laser forwards; a beam barrel located in front of the laser resonator and including at least one lens unit fixed therein; a window barrel located in front of the beam barrel and connected to the main body; a cap part connected to the front of the window barrel and brought into contact with an irradiation target area; a fan unit communicating with the cap part and induce flow of air; and a communication pipe of which one end is connected to the fan unit and the other end is connected to the cap part.

11 Claims, 7 Drawing Sheets

(51) Int. Cl.

| | |
|---|---|
| A61B 18/20 | (2006.01) |
| A61B 18/00 | (2006.01) |
| A61B 90/00 | (2016.01) |
| A61B 5/00 | (2006.01) |
| A61B 18/22 | (2006.01) |
| A61B 17/00 | (2006.01) |
| A61B 17/22 | (2006.01) |

(52) U.S. Cl.
CPC ............ *A61B 2018/00839* (2013.01); *A61B 2018/00904* (2013.01); *A61B 2018/202* (2013.01); *A61B 2018/2023* (2017.05); *A61B 2018/20553* (2017.05); *A61B 2018/2253* (2017.05); *A61B 2090/036* (2016.02); *A61B 2090/049* (2016.02); *A61B 2090/065* (2016.02); *A61B 2217/005* (2013.01); *A61B 2217/007* (2013.01); *A61B 2218/005* (2013.01); *A61B 2218/007* (2013.01); *A61B 2218/008* (2013.01); *A61B 2560/0425* (2013.01); *A61B 2560/0443* (2013.01); *A61B 2560/0462* (2013.01)

(56) References Cited

U.S. PATENT DOCUMENTS

| | | | |
|---|---|---|---|
| 8,394,085 B2 * | 3/2013 | Horikawa | A61B 5/157 |
| | | | 606/17 |
| 2002/0058953 A1 | 5/2002 | Gruzdev et al. | |
| 2002/0133147 A1 * | 9/2002 | Marchitto | A61B 5/411 |
| | | | 606/9 |
| 2009/0275823 A1 | 11/2009 | Ayati et al. | |
| 2014/0257254 A1 | 9/2014 | Boutoussov et al. | |
| 2016/0029937 A1 | 2/2016 | Sia et al. | |
| 2017/0172659 A1 | 6/2017 | Choi | |

FOREIGN PATENT DOCUMENTS

| | | |
|---|---|---|
| EP | 3275392 A1 | 1/2018 |
| JP | S60-063068 A | 4/1985 |
| JP | 2008-522705 A | 7/2008 |
| KR | 10-0989807 B1 | 10/2010 |
| KR | 10-2018-0028241 B1 | 4/2013 |
| KR | 10-2016-0118534 A | 10/2016 |

* cited by examiner

LASER LANCING DEVICE

BACKGROUND OF THE INVENTION

1. Field of the Invention

The present disclosure relates to a laser lancing device.

2. Description of the Conventional Art

Recently, as various medical devices have been developed along with the development of various high technologies, high-tech laser devices are being used more often than ever before in the medical field to treat various diseases.

One of the uses of a medical laser is to perforate skin by irradiating a laser to the skin in order to collect blood from the perforated skin, administer a drug into a perforation, or remove dots or freckles from the skin.

In this regard, Korean Patent No. 10-1251890 (entitled "Portable laser lancing device using dual safety device") discloses a configuration including an irradiation port cover configured to prevent a laser module from outputting a laser to the outside, a first safety switch configured to be turned on and off by up and down movements caused by opening and closing of the irradiation port cover; a second safety switch configured to be turned on and off by an elastic member provided between the laser module and a skin contact part and moved by push and pull movements of the skin contact part, and a button switch configured to allow the laser to be irradiated when both the first safety switch and the second safety switch are turned on.

SUMMARY OF THE INVENTION

The present disclosure provides a laser lancing device which can suck smoke and foreign substance generated during blood collection through a fan unit or relieve pain and heat.

However, problems to be solved by the present disclosure are not limited to the above-described problems. There may be other problems to be solved by the present disclosure.

According to an aspect of the present disclosure, A laser lancing device, comprising: a main body; a laser resonator located within the main body and configured to generate a laser and output the laser forwards; a beam barrel located in front of the laser resonator and including at least one lens unit fixed therein; a window barrel located in front of the beam barrel and connected to the main body; a cap part connected to the front of the window barrel and brought into contact with an irradiation target area; a fan unit communicating with the cap part and induce flow of air; and a communication pipe of which one end is connected to the fan unit and the other end is connected to the cap part.

According to the aspect of the present disclosure, a laser lancing device can suck smoke and foreign substance generated from a treatment area of a patient through a fan unit and can also suppress thermal damage to the treatment area of the patient and relieve pain of the patient, and the laser lancing device can be used continuously for a long time by cooling a laser resonator.

Further, the laser lancing device includes an interlock unit configured to allow a laser to be irradiated to the outside only when a cap part is inserted into a window barrel and thus can keep accidents from occurring.

DETAILED DESCRIPTION OF THE INVENTION

Figure 1:
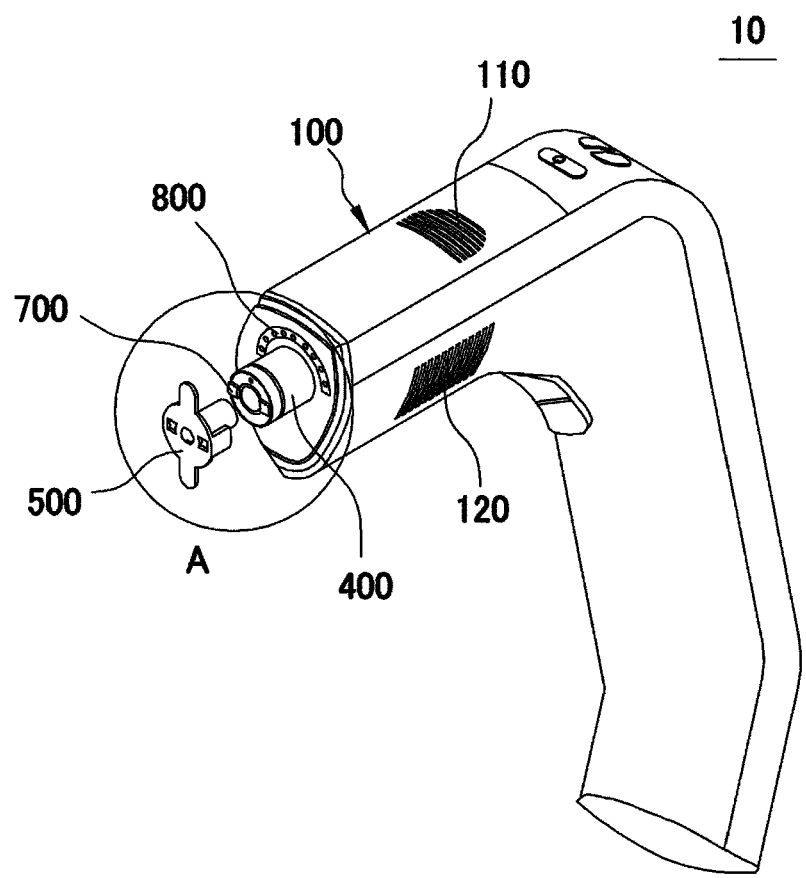
FIG. 1 is a perspective view of a laser lancing device in accordance with an embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

The present disclosure relates to a laser lancing device 10 which can perforate skin using a laser to collect blood.

Figure 2:
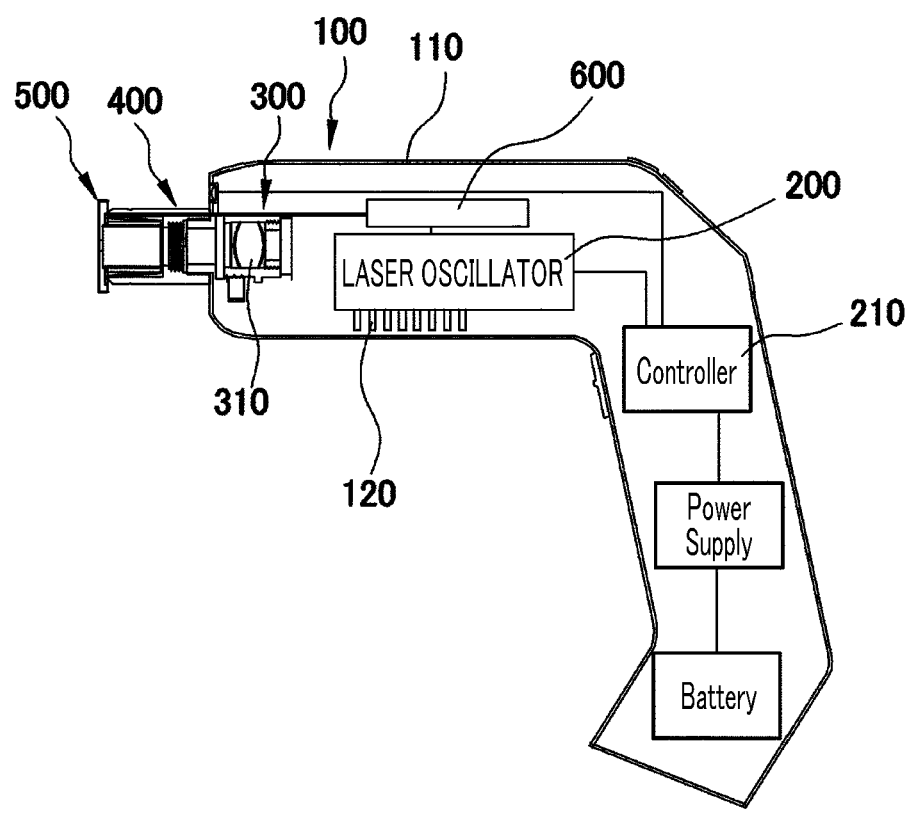
FIG. 2 is a cross-sectional view of the laser lancing device in accordance with an embodiment of the present disclosure.
Figure 3:
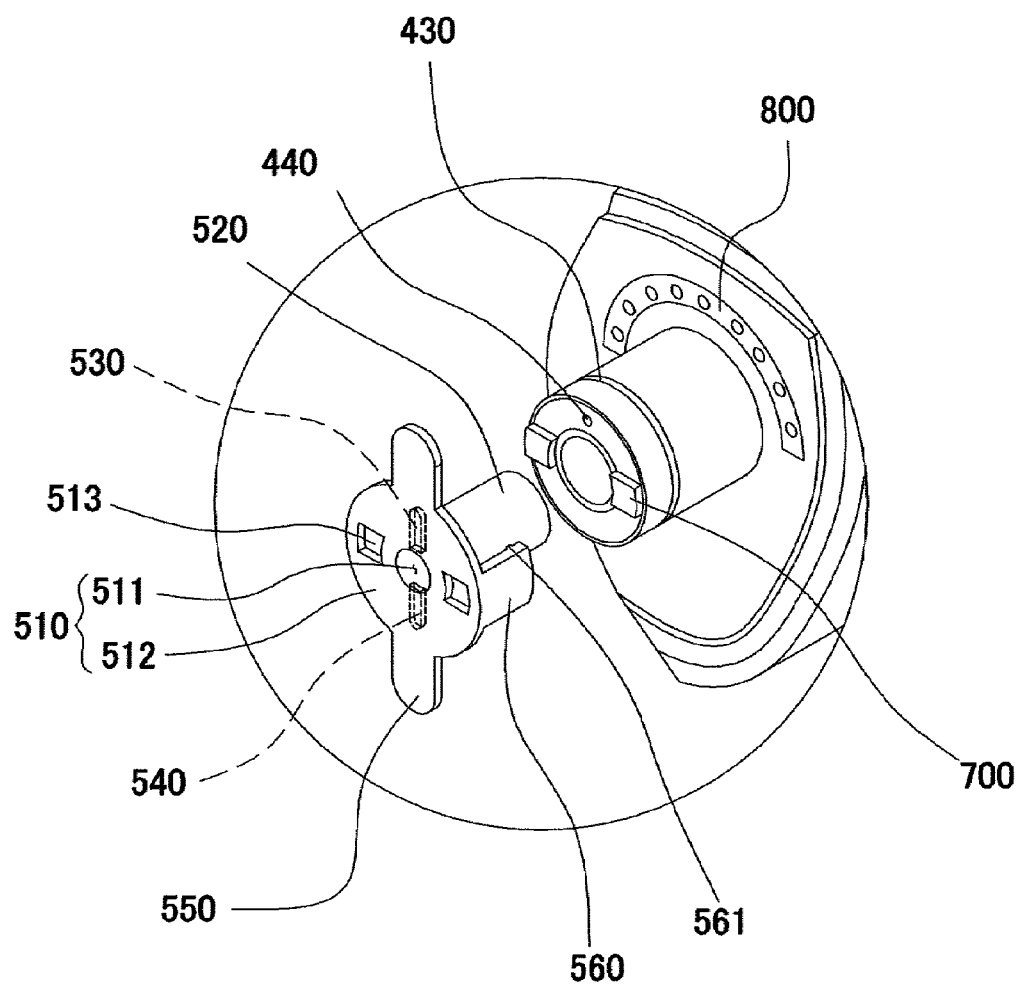
FIG. 3 is an enlarged view of an area A illustrated in FIG. 1.
Figure 4A:
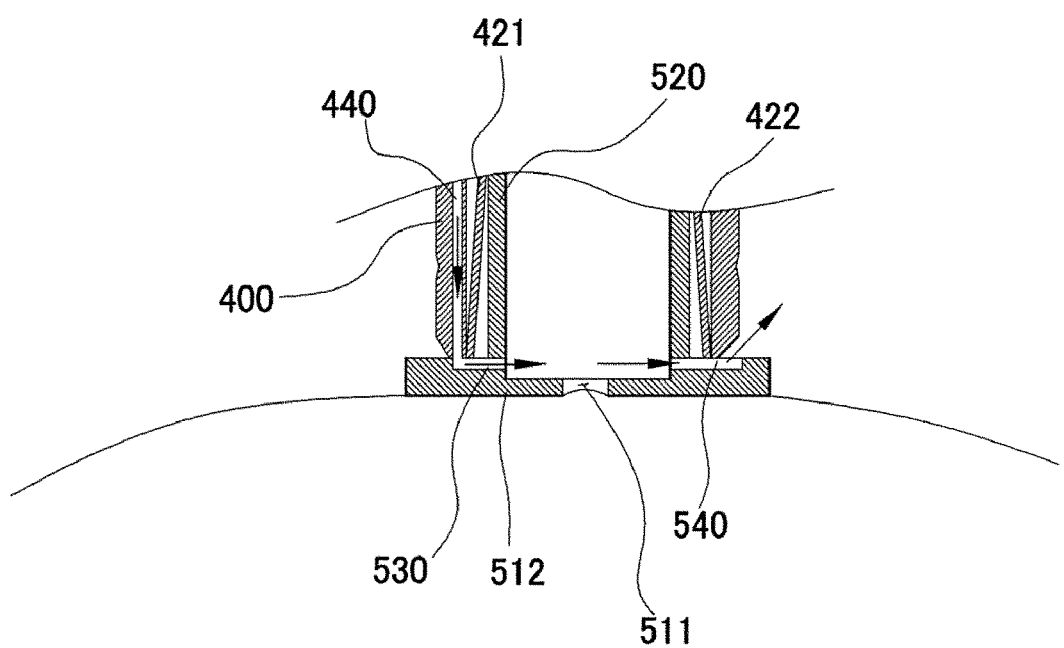
FIGS. 4A and 4B are diagrams provided to explain a fan unit of the laser lancing device in accordance with an embodiment of the present disclosure.
Figure 4B:
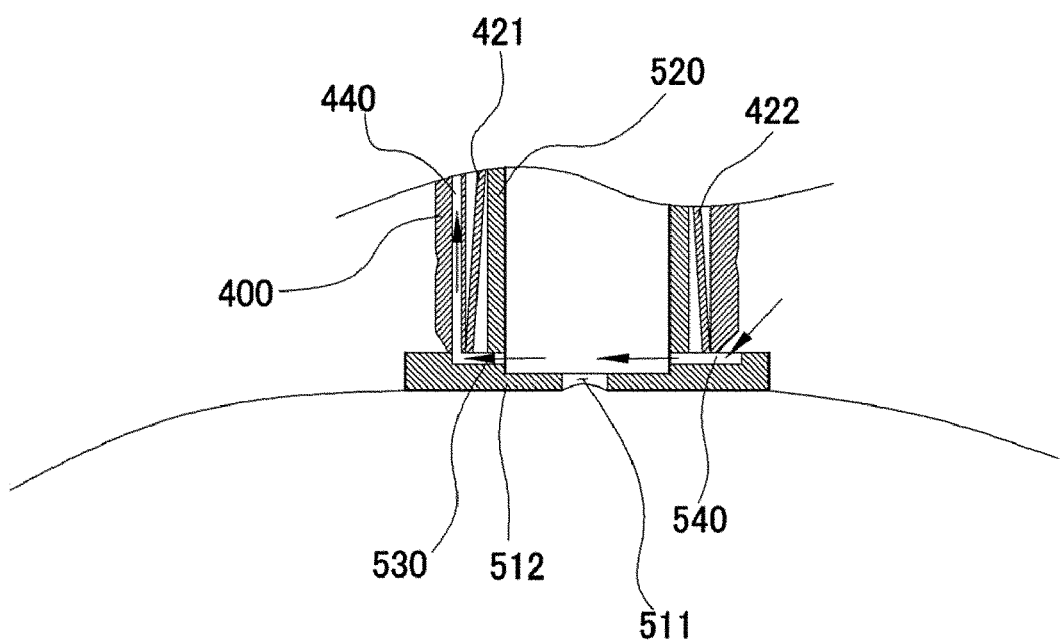
Figure 5A:
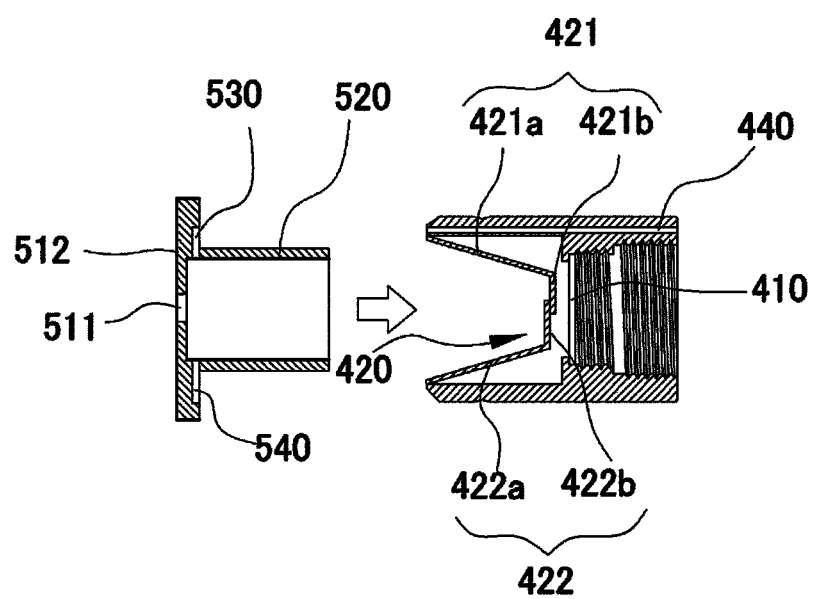
FIGS. 5A and 5B are diagrams provided to explain an interlock unit of the laser lancing device in accordance with an embodiment of the present disclosure.
Figure 5B:
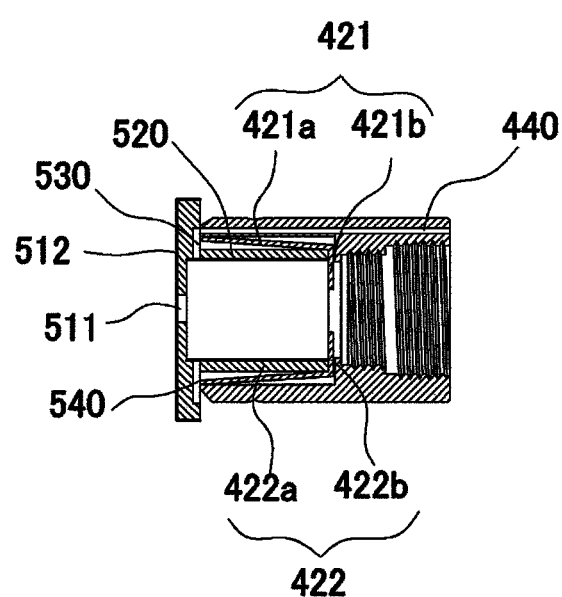

FIG. 1 is a perspective view of the laser lancing device 10 in accordance with an embodiment of the present disclosure, FIG. 2 is a schematic diagram of the laser lancing device 10 in accordance with an embodiment of the present disclosure, FIG. 3 is an enlarged view of an area A illustrated in FIG. 1, FIGS. 4A and 4B are diagrams provided to explain a fan unit 600 of the laser lancing device 10 in accordance with an embodiment of the present disclosure, and FIGS. 5A and 5B are diagrams provided to explain an interlock unit 420 of the laser lancing device 10 in accordance with an embodiment of the present disclosure.

Referring to FIG. 1 to FIG. 3, the laser lancing device 10 according to an embodiment of the present disclosure will be described first.

The laser lancing device 10 may include a main body 100, a laser resonator 200, a beam barrel 300, a window barrel 400, a cap part 500, and the fan unit 600.

The main body 100 includes therein a component configured to irradiate a laser to an irradiation target area and may be formed for a user to grip.

The laser resonator 200 is located within the main body 100 and configured to generate light energy and output the light energy forwards. For example, the laser resonator 200 may be supplied with electric energy and may amplify light to generate light energy such as a laser selected from a gas laser, a liquid laser, a solid laser, and a semiconductor laser and then output the light energy to the outside.

The beam barrel 300 may be in front of the laser resonator 200 and may include at least one lens unit 310 fixed therein. For example, the lens unit 310 may be a focusing lens, but may not be limited thereto.

The window barrel 400 may be in front of the beam barrel 300 and connected to the main body 100. For example, the window barrel 400 may be in front of the beam barrel 300 and may include a hole perforated in a forward and backward direction and a screw thread at the back of its inner periphery and thus can be screw-connected to the main body 100, as illustrated in FIG. 5A. Further, the window barrel 400 may include therein a window part 410 to suppress penetration of foreign substance, such as dust, into the main body 100. In this case, desirably, the window part 410 may be manufactured using a transparent material in order to irradiate a laser passing through the beam barrel 300 toward the front of the window barrel 400.

Further, referring to FIG. 5A, the window barrel 400 may include a communication pipe 440 through which a cooling medium to be supplied to the cap part 500 passes or smoke or foreign substance generated in the cap part 500 is sucked. In other words, one end of the communication pipe 440 is connected to the fan unit 600 and the other end thereof is connected to a first communication hole 530 of the cap part 500, and, thus, a cooling medium of the fan unit 600 can be supplied to the cap part 500 or smoke or foreign substance generated in the cap part 500 can be sucked through the first communication hole 530. Details thereof will be described later.

The cap part 500 may be connected to the front of the window barrel 400 and brought into contact with an irradiation target area.

For example, the cap part 500 may be replaceably connected to the front of the window barrel 400. Further, the cap part 500 may be brought into contact with an irradiation target area and may minimize smell, smoke, or noise generated during perforation of the irradiation target area. For example, the irradiation target area may be the skin of a patient. Moreover, it is possible to suppress infection between patients sharing the laser lancing device 10 by replacing the cap part 500 for each user.

The fan unit 600 is configured to supply the cooling medium to the laser resonator 200 and the cap part 500. In this case, external air may be used as the cooling medium. Further, the laser lancing device 10 may include the communication pipe 440 of which one end is connected to the fan unit 600 and the other end is connected to the cap part 500.

For example, in the case where external air is used as the cooling medium, the fan unit 600 may include a cooling fan and supply the external air directly to the laser resonator 200 by driving the cooling fan and then to the cap part 500 through the communication pipe 440.

Specifically, referring to FIG. 1, the main body 100 may include an air inlet port 110 through which external air is supplied to the fan unit 600 and an air outlet port 120 through which the air introduced through the air inlet port 110 is discharged to the outside. Further, the fan unit 600 may supply air supplied through the air inlet port 110 to the laser resonator 200 and discharge air cooling the laser resonator 200 to the outside through the air outlet port 120. Furthermore, the air introduced through the air inlet port 110 may be supplied to the cap part 500 through the communication pipe 440. Moreover, the air supplied to the cap part 500 may cool the skin of a user. Details thereof will be described later.

The laser lancing device 10 may further include a vane finder 800 located in front of the main body 100 and configured to irradiate light to skin to reveal the location of a blood vessel. The vane finder 800 is configured to irradiate near-infrared rays to the skin of a patient to clearly reveal a blood vessel of the patient. In other words, the laser lancing device 10 uses the vane finder 800 to enable a user to easily find a blood vessel of a patient and thus irradiate a laser to a correct position.

The laser lancing device 10 may further include a forward and backward moving means (not illustrated) configured to move the beam barrel 300 forwards and backwards. In other words, the forward and backward moving means may move the beam barrel 300 forwards and backwards to adjust a distance between the skin of a patient and the focusing lens and thus adjust a spot size of a laser irradiated to the skin of the patient. For example, when the spot size of the laser is adjusted by the user using a controller, a motor may be driven to adjust a location of the beam barrel 300, but the present disclosure may not be limited thereto. A location of the beam barrel 300 may also be moved manually in a forward and backward direction.

The cap part 500 according to an embodiment of the present disclosure will be described in detail with reference to FIG. 3, FIGS. 4A and 4B.

The cap part 500 may include a cap main body 510, a through hole 520, the first communication hole 530, and a second communication hole 540.

The cap main body 510 may include an opening 511 and a supporting surface 512 to be supported on a contact point along the periphery of the opening 511. For example, the cap main body 510 may be formed into a circular plate shape including the opening 511 at the center, as illustrated in FIG. 3. The cap main body 510 may further include at least one handgrip 550 formed and extended from the supporting surface 512 of the cap main body 510. The user may easily attach and detach the cap part 500 to and from the laser lancing device 10 using the handgrip 550. However, the present disclosure may not be limited thereto, and the laser lancing device 10 may further include a separate ejector to attach and detach the cap part 500.

A designer can determine the size of the opening 511, but it is desirable to secure an enough size to secure a travel path of a laser output from the laser lancing device 10 in order for the laser not to be affected by the through hole 520 of the cap part 500. Further, it is desirable to design the opening 511 to have a size smaller than an average size of the tip of a finger mainly in contact with the cap part 500 and thus to provide an appropriate pressure to a contact area. Likewise, the supporting surface 512 is designed to have a size enough for the cap part 500 to be in close contact with a contact point.

Further, the cap part 500 may include a clamping unit 560 connected to the cap main body 510 and connecting the cap main body 510 to the window barrel 400 of the laser lancing device 10. For example, the clamping unit 560 may be located on the periphery of the back side of the cap part 510, protruding backwards, and include a protruding part 561 formed on an inner surface. Furthermore, the protruding part 561 may be engaged with a clamping groove 430 formed on the periphery of the window barrel 400 to suppress an unintended separation of the cap part 500.

The through hole 520 is formed and extended from the back side of the opening 511 of the cap main body 510 and has a predetermined space therein.

Referring to FIG. 3, FIG. 4A and FIG. 4B, the first communication hole 530 may be formed to enable communication between the communication pipe 440 and the inside of the through hole 520 and the second communication hole 540 may be formed to enable communication between the inside and the outside of the through hole 520.

Specifically, referring to FIG. 4A, if an irradiation target area is cooled using the fan unit 600, a cooling medium supplied through the communication pipe 440 may be supplied to the inside of the through hole 520 through the first communication hole 530 of the cap part 500. Further, the cooling medium supplied to the inside of the through hole 520 may be used to cool the irradiation target area located at the opening 511 of the cap main body 100 and then discharged to the outside through the second communication hole 540. Furthermore, if external air is used as the cooling medium, it is possible to simplify the configuration and also possible to suppress damage to the device caused by leakage of a cooling medium.

Further, referring to FIG. 4B, if smoke and foreign substance generated during blood collection is sucked using the fan unit 600, the fan unit 600 generates suction force and the smoke and the foreign substance can be removed through the communication pipe 440 and the first communication hole 530 communicating with the fan unit 600. For example, external air introduced through the second communication hole 540 may pass through the irradiation target area and may be introduced into the communication pipe 440 through the first communication hole 530 together with smoke and foreign substance located in the irradiation target area, and the irradiation target area may be cooled by the air introduced through the second communication hole 540.

Referring to FIG. 3, the laser lancing device 10 may further include a contact sensor 700 located in front of the window barrel 400, and the cap main body 510 may include a sensor hole 513 through which the contact sensor 700 penetrates. Further, the laser lancing device 10 allows a laser to be irradiated when the contact sensor 700 senses a contact with the irradiation target area and thus can keep accidents from occurring. For example, the contact sensor 700 may be one of a current sensor configured to detect a micro-current flowing in the human body and a temperature sensor configured to detect a temperature of an irradiation target area in contact with the sensor.

The interlock unit 420 according to an embodiment of the present disclosure will be described in detail with reference to FIG. 5A and FIG. 5B.

The window barrel 400 may include the interlock unit 420 configured to block or open a path through which a laser passes. Further, the interlock unit 420 may open the laser path when the cap part 500 is inserted into the window barrel 400.

Specifically, the interlock unit 420 may include a first block unit 421 including a first plate 421a of which one end is connected to a front end of the window barrel 400 and which is formed and extended at a predetermined angle toward a central portion of the window barrel 400 and a first bent portion 421b formed by bending the other end of the first plate 421a toward the laser path, and a second block unit 422 including a second plate 422a of which one end is connected to the front end of the window barrel 400 and which is formed and extended at a predetermined angle toward the central portion of the window barrel 400 and a second bent portion 422b formed by bending the other end of the second plate 422a toward the first bent portion 421b. For example, the first plate 421a and the second plate 422a may be bent with the same curvature as an outer circumference surface of the through hole 520.

In other words, referring to FIG. 5A, the interlock unit 420 is located within the window barrel 400, and the first bent portion 421b and the second bent portion 422b are in the laser path through which a laser passes. Thus, it is possible to suppress irradiation of a laser to the outside when the cap part 500 is not used.

Further, the interlock unit 420 may open the laser path when the cap part 500 is inserted into the window barrel 400. Specifically, when the through hole 520 of the cap part 500 is inserted into the window barrel 400, an end portion of the through hole 520 of the cap part 500 is brought into contact with the first plate 421a and the second plate 422a, and, thus, the first plate 421a and the second plate 422a can be moved toward the outside of the window barrel 400. In this case, the first bent portion 421b and the second bent portion 422b are moved toward the outside of the window barrel 400 and separated from each other. Therefore, a path through which a laser is irradiated can be opened between the first bent portion 421b and the second bent portion 422b. Accordingly, when the cap part 500 is not used, the laser lancing device 10 can suppress irradiation of a laser to the outside and thus keep accidents from occurring.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A laser lancing device, comprising:
   a main body;
   a laser resonator located within the main body and configured to generate a laser and output the laser forwards;
   a beam barrel located in front of the laser resonator and including at least one lens unit fixed therein;
   a window barrel located in front of the beam barrel and connected to the main body;
   a cap part connected to the front of the window barrel and brought into contact with an irradiation target area;
   a fan unit communicating with the cap part and induce flow of air; and
   a communication pipe of which one end is connected to the fan unit and the other end is connected to the cap part, wherein the cap part includes:

a cap main body including an opening and a supporting surface to be supported on a contact point along the periphery of the opening;

a through hole formed and extended from the back side of the opening of the cap main body, inserted into the window barrel, and having a predetermined space therein;

a first communication hole formed to enable communication between the communication pipe and the inside of the through hole; and a second communication hole formed to enable communication between the inside and the outside of the through hole.

2. The laser lancing device of claim 1,
wherein the fan unit sucks smoke or foreign substance generated in the cap part using the communication pipe.

3. The laser lancing device of claim 1,
wherein the fan unit supplies a cooling medium to the cap part through the communication pipe.

4. The laser lancing device of claim 1, further comprising:
a contact sensor located in front of the window barrel,
wherein the cap main body includes a sensor hole through which the contact sensor penetrates.

5. The laser lancing device of claim 1,
wherein the cap part further includes a clamping unit connected to the cap main body and connecting the cap main body to the window barrel.

6. The laser lancing device of claim 1,
wherein the cap part further includes a handgrip formed and extended from the supporting surface of the cap main body.

7. The laser lancing device of claim 1,
wherein the main body includes:
an air inlet port through which external air is supplied to the fan unit; and
an air outlet port through which the air introduced through the air inlet port is discharged to the outside.

8. The laser lancing device of claim 1,
wherein the window barrel includes an interlock unit configured to block or open a path through which the laser passes, and the interlock unit opens the laser path when the cap part is inserted into the window barrel.

9. The laser lancing device of claim 8,
wherein the interlock unit includes:
a first block unit including a first plate of which one end is connected to a front end of the window barrel and which is formed and extended at a predetermined angle toward a central portion of the window barrel and a first bent portion formed by bending the other end of the first plate toward the laser path; and
a second block unit including a second plate of which one end is connected to the front end of the window barrel and which is formed and extended at a predetermined angle toward the central portion of the window barrel and a second bent portion formed by bending the other end of the second plate toward the first bent portion, and
when the cap part is inserted into the window barrel, the first block unit and the second block unit are moved and separated from each other to open a path through which the laser is irradiated between the first block unit and the second block unit.

10. The laser lancing device of claim 1, further comprising:
a vein finder located in front of the main body and configured to irradiate light to the irradiation target area to reveal the location of a blood vessel.

11. The laser lancing device of claim 1, further comprising:
a forward and backward moving means configured to move the beam barrel forwards and backwards.

* * * * *